United States Patent [19]

Paulson, Jr. et al.

[11] Patent Number: 4,521,111
[45] Date of Patent: Jun. 4, 1985

[54] APPARATUS FOR MEASUREMENT OF MOLECULAR ORIENTATION

[75] Inventors: Charles M. Paulson, Jr.; Mark E. Faulhaber, both of Wilmington, Del.

[73] Assignee: E. I. Du Pont de Nemours and Company, Wilmington, Del.

[21] Appl. No.: 401,331

[22] Filed: Jul. 23, 1982

[51] Int. Cl.³ .............................................. G01J 4/04
[52] U.S. Cl. ................. 356/367; 250/461.1; 356/429
[58] Field of Search ............... 356/317, 364, 368, 369, 356/429, 367; 250/461.1, 559, 521, 225

[56] References Cited

U.S. PATENT DOCUMENTS

| | | | |
|---|---|---|---|
| 3,525,871 | 8/1970 | Lehtinen | 250/219 |
| 3,679,309 | 7/1972 | Hiragaki et al. | 356/114 |
| 3,759,618 | 9/1973 | Rogers et al. | 356/364 X |
| 3,914,057 | 10/1975 | Smith et al. | 356/118 |
| 3,955,096 | 5/1976 | Faulhaber | 250/565 |
| 4,140,902 | 2/1979 | Young | 250/225 |
| 4,264,207 | 4/1981 | Batyrev et al. | 356/364 |

OTHER PUBLICATIONS

J. Lavorel et al., A New Method of Fluorescence Polarization Measurement, Biochimie (1972) 54, 161–165.

Primary Examiner—Davis L. Willis
Assistant Examiner—Matthew W. Koren

[57] ABSTRACT

An apparatus for measuring the degree and direction of molecular orientation in film as it advances from a stretching zone. The apparatus includes a detection circuit which receives synchronous and sinusoidal reference and analytical signals based on a beam of rotating linearly polarized light.

4 Claims, 18 Drawing Figures

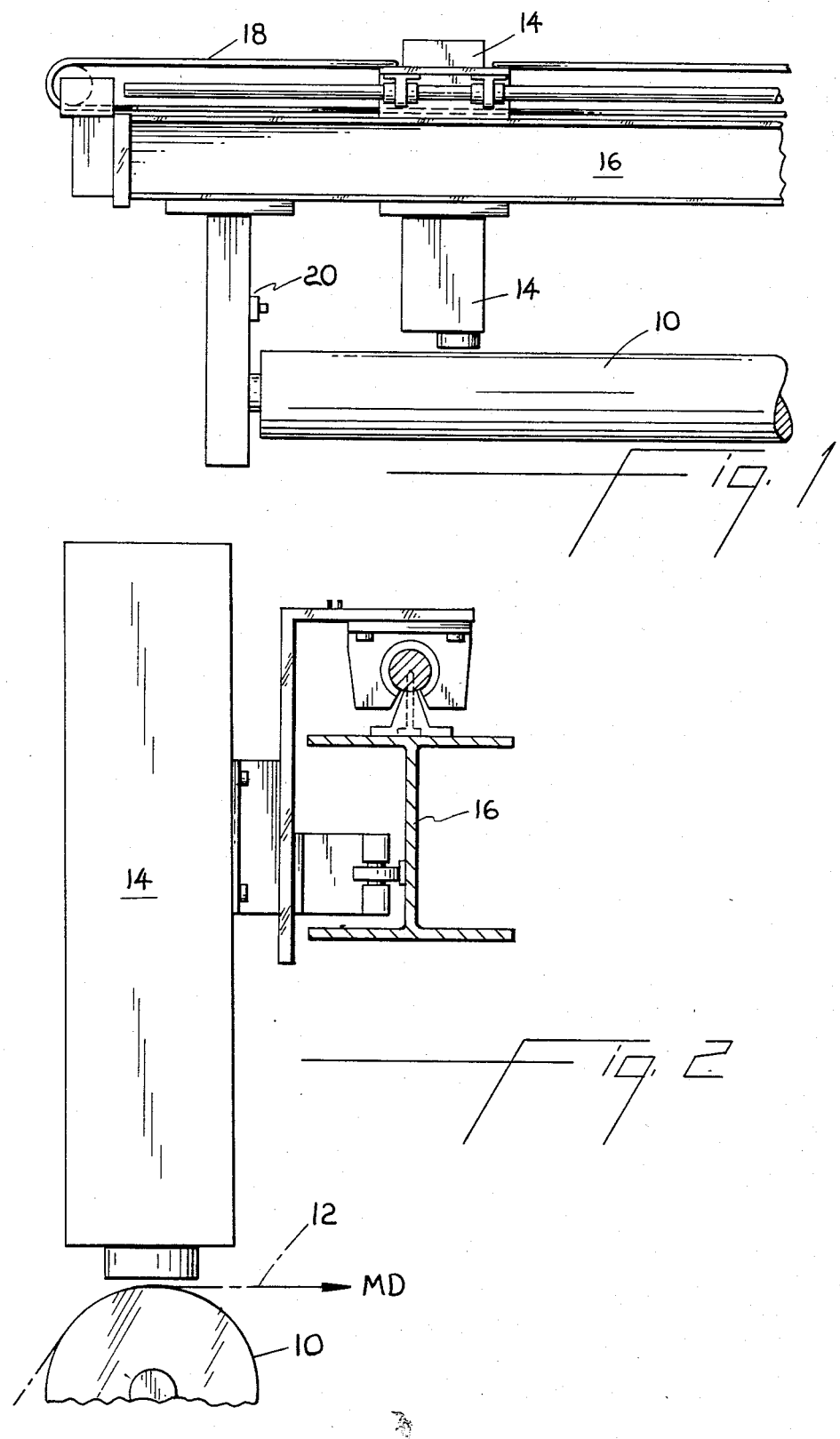

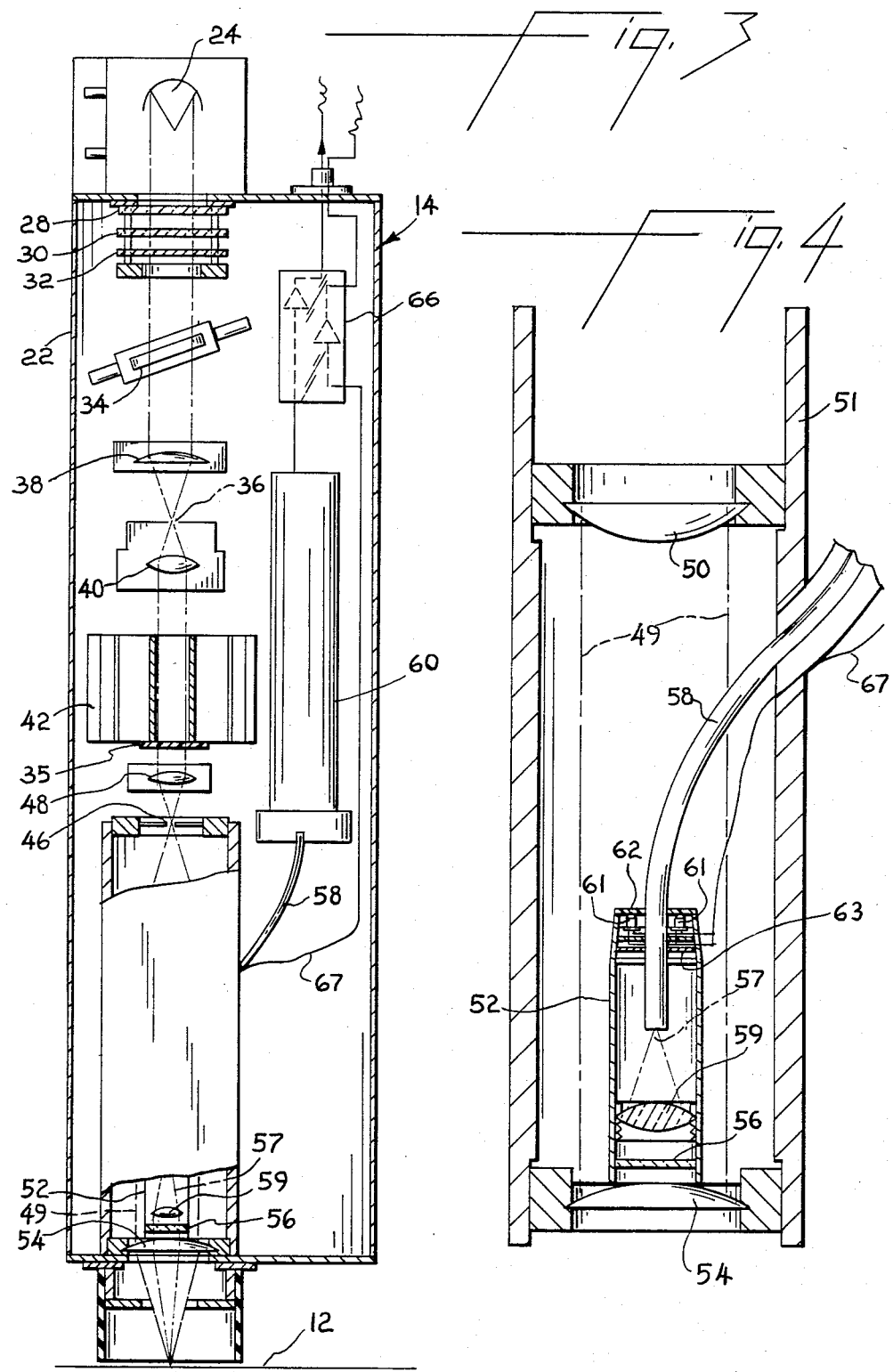

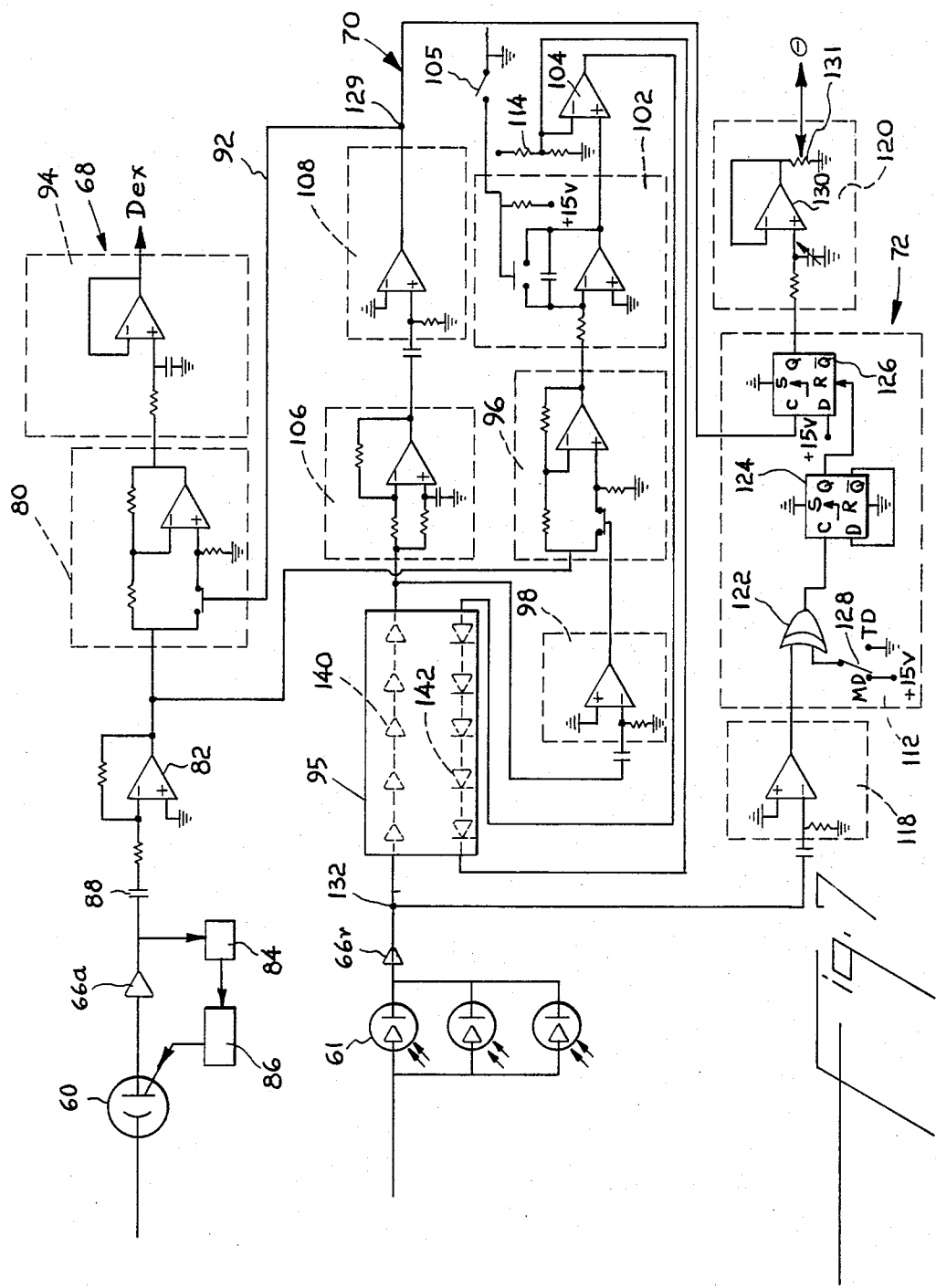

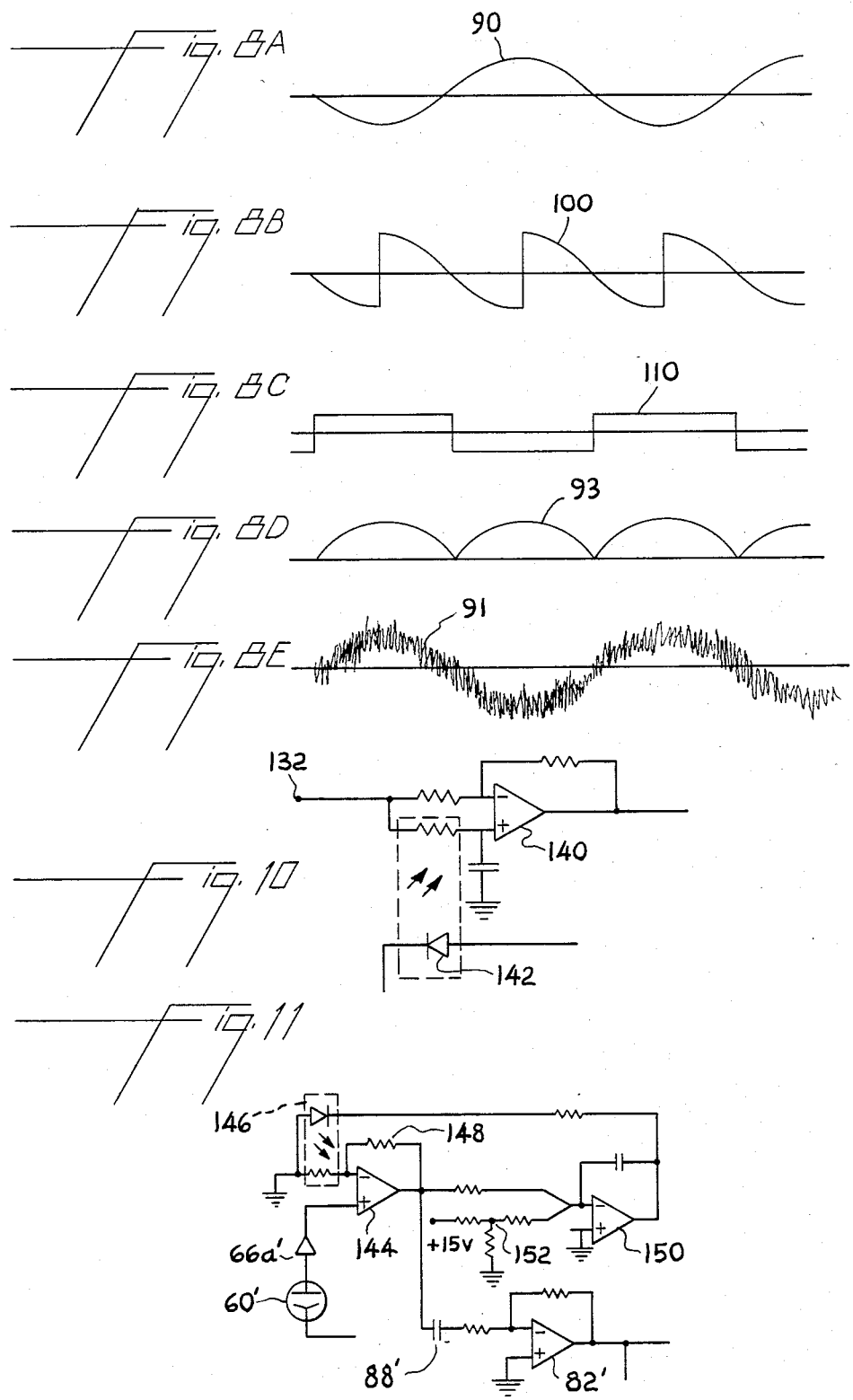

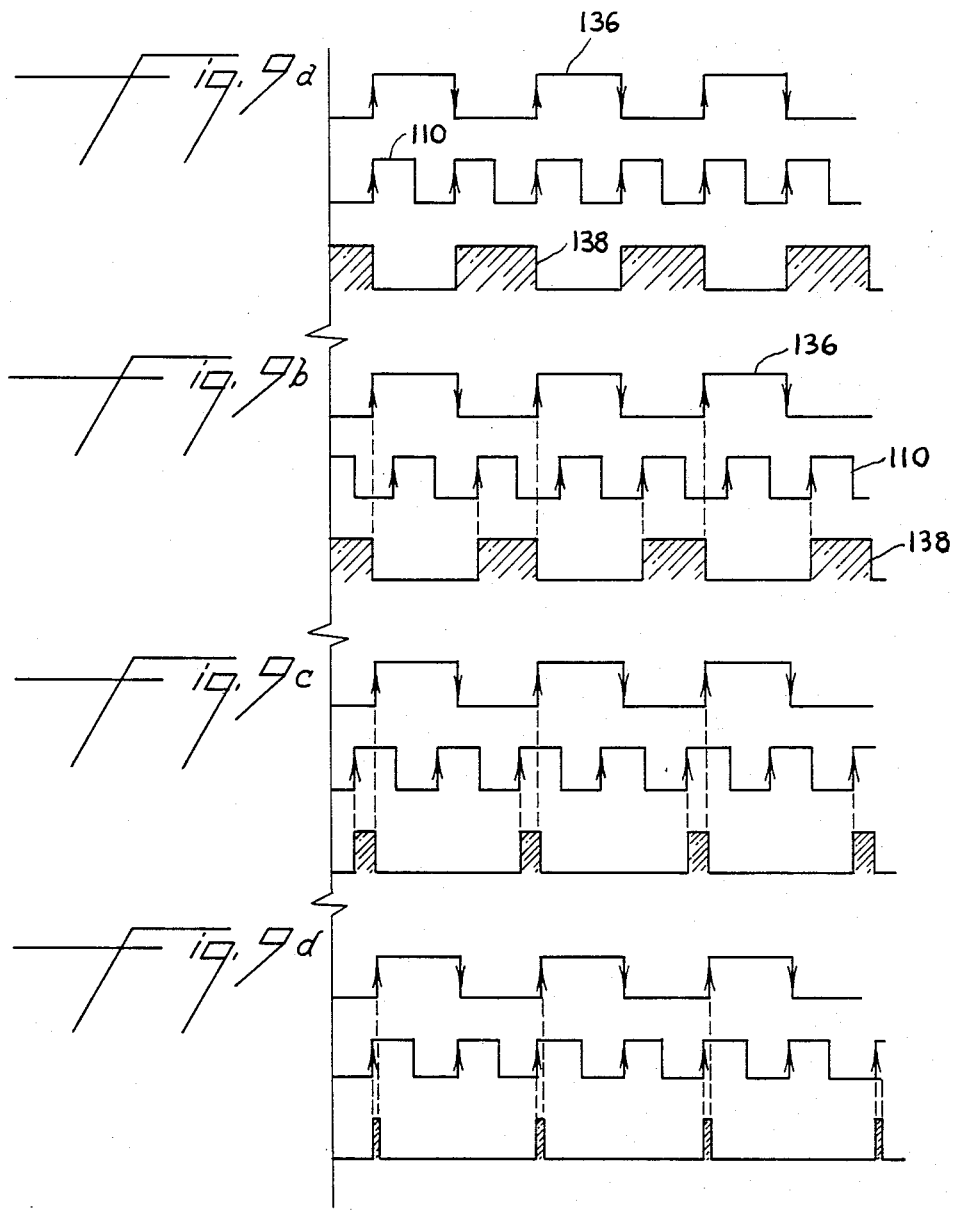

APPARATUS FOR MEASUREMENT OF MOLECULAR ORIENTATION

BACKGROUND

This invention relates generally to the measurement of molecular orientation in polymeric products and, more particularly, to apparatus for detecting and analyzing variations of fluorescence in a product as it is moved through an incident beam of rotating, linearly polarized light.

It is known in the art that information pertinent to the molecular orientation of polymeric products can be obtained by detecting the intensity of fluorescent radiation emitted from a sample excited by polarized light. Attempts to use available instruments for the on-line inspection of polymeric products such as film, e.g., after the first of two coupled stretching steps, have not been successful for a number of reasons. Where the light source and fluorescence detector are on opposite sides of a film, scanning through a wide sample is difficult and, of course, impossible with opaque films. Where the excitation and emission beams are located on the same side of a sample, they have been disposed angularly and that relationship introduces a bias in measurements of intensity. Although orientation can be determined as a function of birefringence, that measurement is dependent on optical retardation, a function of film thickness. Since thickness must be measured simultaneously with retardation, on-line inspections are not practicable. Instead, it is usually the practice to stop a production line and take a sample in order to obtain information as to the birefringence of a partially processed film. That information must then be related to the finished product by extrapolation.

Another difficulty with available instruments is that the analysis of fluctuating, periodic, sinusoidal signals is complicated by broad-band noise components which originate from sources such as mechanical vibration, photomultiplier tube shot-noise, and stray light from outside the instrument. These effects obscure an accurate measurement of both the degree and direction of molecular orientation in continuously advancing products. In fact, the sinusoidal signals to be measured not only may have amplitude levels below the level of the background noise but also have phase and amplitude characteristics that vary randomly. Such factors have made it practically impossible to relate the axes of fluorescence maxima and minima to the direction of polymer chains.

SUMMARY

The above and other difficulties have been overcome with an apparatus having means for establishing a beam of rotating linearly polarized light which passes around an emission housing and is incident on the location of a product to be inspected. A first photodetector has a light sensitive element in the path of incident light passing through a polarizer affixed to the housing. There is a filter in the housing in the path of emitted light. A second photodetector has a light sensitive element in the optical path of emitted, filtered light. The photodetectors provide synchronous and sinusoidal reference and analytical signals to a detection circuit.

In the detection circuit, first circuitry adjusts the phase of the reference signal into agreement with the phase of the analytical signal and second circuitry synchronously demodulates the analytical signal. The reference signal is an input to the first circuitry and the analytical signal is an input to each of the circuitries. The second circuitry also receives the phase-adjusted output of the first circuitry as a gating input. There is, in addition, third circuitry for measuring the phase difference between the reference signal and the phase-adjusted reference signal. The outputs of the second and third circuitries, i.e., the detected signal and the phase adjustment needed to obtain it, characterize the extent and direction of molecular orientation in the inspected product.

DRAWINGS

Additional objectives and advantages will be apparent from the following description wherein reference is made to the accompanying drawings in which:

FIGS. 1 and 2 are fragmentary illustrations of a traversing instrument and its association with a film path;

FIGS. 3 and 4 are enlarged, sectional views of the instrument shown in FIGS. 1 and 2;

FIG. 7 is a detailed diagram of the circuitries shown in FIG. 5;

Figure 5:
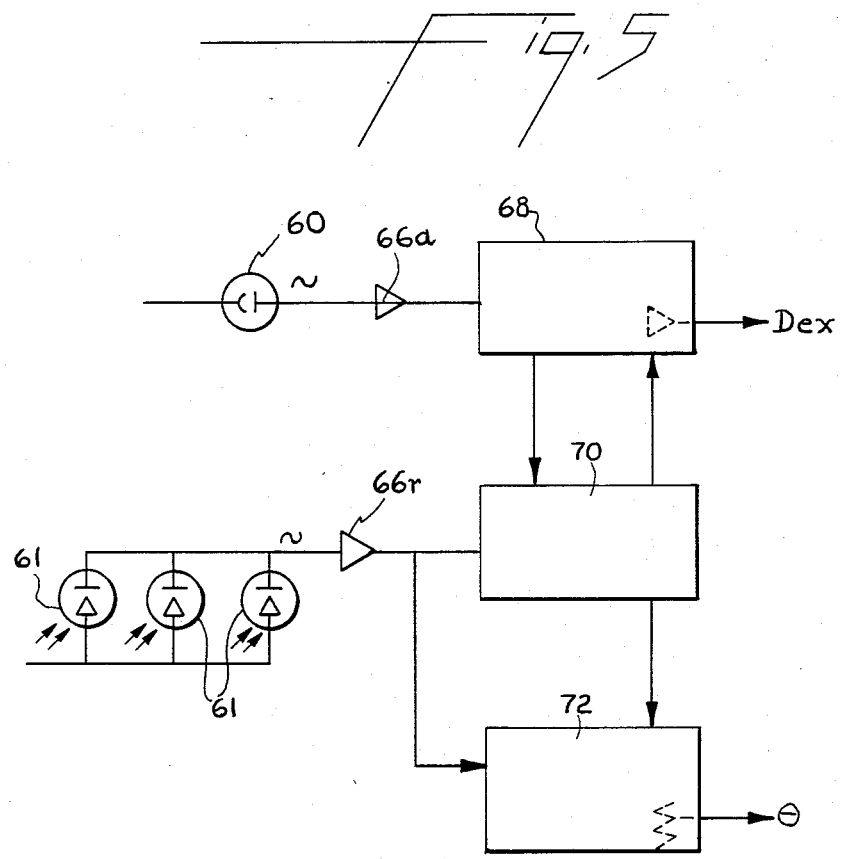
FIG. 5 is a block diagram of a detection circuit for analyzing outputs of the instrument.

FIGS. 8 A–E are schematic representations of typical waveforms at different locations in the circuitries of FIG. 7;

FIGS. 9 A–D are schematic representations of waveforms at different locations in a phase-measuring circuitry shown in FIGS. 5 and 7;

FIG. 10 is a detailed illustration of one of the multiple stages of phase-shifting shown schematically in FIG. 7; and FIG. 11 is a diagram of a modification of the circuit shown in FIG. 7.

DESCRIPTION OF APPARATUS

The installation shown in FIGS. 1 and 2 includes a transfer roll 10 over which a biaxially-stretched film 12 is advanced to be packaged. Above roll 10, the optical head 14 of an instrument for measuring the intensity of fluorescence is slidably mounted on a beam 16. Head 14 is connected to the ends of an otherwise continuous chain 18 which traverses it with respect to roll 10. Reversals are determined by contacts between head 14 and limit switches 20 located adjacent each end of the roll.

As shown in FIGS. 3 and 4, the optical elements of the instrument are mounted in or on a support housing 22. Ultraviolet (UV) light from a lamp 24 is directed into housing 22 through a broad-band UV interference filter 28, a UV-transmitting visible-absorbing filter 30 and a narrow-band interference filter 32. Filter 28 protects the remaining elements in the optical train from excessive infrared (IR), visible and UV radiations outside the excitation wavelength (λex) of interest. Filter 30 reduces stray light at the emission wavelength of interest (λem) and filter 32 limits the incident radiation to λex. The next element is a quartz plate 34 that can be positioned to correct for fluctuations in intensity of the beam as a linear polarizer 35 is rotated. The beam is focused at an aperture 36 by a lens 38 and then collimated by a lens 40 so as to pass through the hollow center of a high speed synchronous motor 42. Linear polarizer 35 is a UV-transmitting, polarizing film and is attached to the end of the rotor of motor 42 by a press-fit, in covering relationship to its hollow center. Light passing through rotary polarizer 35 is focused at aperture 46 by a lens 48 and collimated to a larger beam 49 by a lens 50. Lens 50 and the collimated beam are within an enclosure 51. The incident beam of rotating, linearly polarized light passes around an inner, emission housing 52 and is focused on the product being inspected by a lens 54. In FIGS. 2 and 3, the product is film 12.

Fluorescence is excited in film 12 by absorption at λex. The emitted light is collimated by lens 54, passes through an emission filter 56 and is focused at 57 on the end of a light guide 58 by a lens 59. Filter 56 has a pass-band centered on λem and, therefore, excludes reflected incident light. The other end of light guide 58 discharges onto the light sensitive element of a photomultiplier tube (PMT) 60. Thus, guide 58 functions as a pickup for emitted light. Filter 56, lens 59 and the pickup end of light guide 58 are shielded from incident light by inner, emission housing 52.

Within housing 52, there is an equiangularly-spaced array of three photodiodes 61 connected in parallel. Each photodiode 61 has a light sensitive element that is exposed to the polarized excitation beam 49 through a UV-transparent polarizing film 62, i.e., photodiodes 61 are scanned at the same frequency as film 12. Passage of incident light to the lower regions of housing 52 is prevented by an opaque plate 63 (FIG. 4). The light sensitive elements of photodiodes 61 function as direct pickups for the incident, polarized light. Film 62 is positioned on the otherwise open top of housing 52 with its polarizing direction fixed parallel to the film path, i.e., in the machine direction (MD). Thus, photodiodes 61 provide a synchronous, sinusoidal reference signal to the detection circuitry shown in FIG. 5 and this reference sinusoid peaks positively when rotary polarizer 35 is aligned with MD. The analytical signal from PMT 60 is connected to a preamplifier stage 66. The reference signal from the array of photodiodes 61 is connected to stage 66 by a conductor 67.

Figure 6:
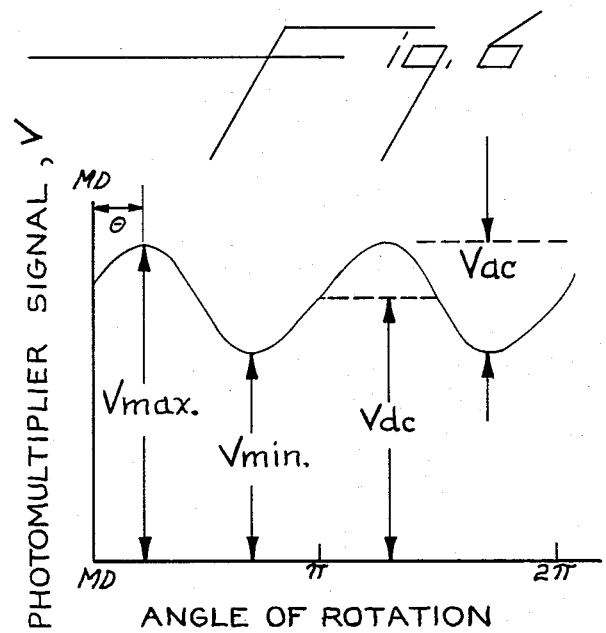
FIG. 6 is a graph showing relationships between voltages in the fluctuating output of the photomultiplier tube shown in FIGS. 3 and 5.

Referring now to the block diagram in FIG. 5, the preamplified signal from PMT 60 and amplifier 66a is an input to a synchronous detector in a ratio-measuring circuitry 68. Signal rectification and averaging stages in circuitry 68 yield a time-base averaged, direct current signal related to the extent of orientation (Dex) in stretched film 12. As shown in FIG. 6, the output of PMT 60 is an alternating current (ac) signal superimposed on a direct current (dc) signal. The illustrated sinusoid is 90° out of phase with the reference sinusoid. The waveform represents one turn of the rotor in motor 42. Consequently, its frequency is twice that of the rotating polarizer 35. The parameter Dex correlates well with standard measurements of molecular orientation, such as birefringence, and has been defined $$Dex = 2\frac{(Vmax - Vmin)}{(Vmax + Vmin)} = \frac{Vac}{Vdc}$$

After further amplification in circuitry 68, the fluctuating output of PMT 60 is routed to a phase-shifting circuitry 70 where it is demodulated and used to adjust the phase of the sinusoidal reference signal from photodiodes 61 and amplifier 66r into agreement with the phase of the PMT output signal. The phase-adjusted signal provides a switching time-base for ratio-measuring circuitry 68 and a clean waveform for analysis in a phase-measuring circuitry 72. In circuitry 72, the phases of the phase-adjusted reference signal and the reference signal itself are compared and a dc signal representative of the direction of molecular orientation (θ) is generated.

Details of circuitries 68, 70, 72 are described below with reference to FIGS. 7–10.

With film 12 advancing continuously over roll 10 and under optical head 14, the instrument is placed in operation by energizing lamp 24, motor 42, the drive for chain 18, the power supply to PMT 60 and circuitries 68, 70, 72 and related equipment such as a strip chart for recording Dex and θ. In a test embodiment, transfer roll 10 was covered with a black, nonreflective, nonfluorescing paper. The optical head scans continuously while traversing film 12 in one direction and is reversed by engagement of head 14 with a limit switch 20 at one end of roll 10. A typical scanning speed is five meters/minute. Another scanning traverse is initiated by engagement of head 14 with the limit switch 20 at the other end of roll 10.

For the examination of films of polyethylene terephthalate, interference filter 32 has a peak transmission at 340 nanometers (nm) and emission filter 56 a peak transmission at 390 nm. Lamp 24 is a 150 watt xenon lamp (VIX–150 UV, Varian/Eimac Division). Films 35, 62 are UV-transmitting, linear polarizers (HNP′B, Polaroid). PMT 60 is a commercially available photomultiplier tube (9824A, EMI). Light guide 58 is a clad glass rod (CR2-12, American Optical). Photodiodes 61 are pn junction semiconductors (VTB 1113, Vactec, Inc.). Typically, motor 42 (0427-11, Sawyer Ind., Inc.) is operated at a speed of about 30,000 revolutions/minute (rpm), thus producing a frequency of about 1,000 hertz (Hz) in the ac component of the PMT signal and in the synchronous reference signal.

UV radiation from lamp 24 is filtered at 28, 30, 32 to isolate the excitation wavelength (λex) of interest. The beam is narrowed at 38, 40, passes through the hollow shaft of motor 42 and is then enlarged at 48, 50 to the collimated beam 49 of rotating, polarized light. Beam 49 passes around emission housing 52 and is focused onto film 12 by lens 54.

As is apparent from the foregoing, the instrument is usually mounted to traverse the width of a film. It measures and plots Dex and θ against transverse position with respect to the film, thus providing a continuous record of both the extent and direction of molecular orientation. The instrument can also be stopped at any position across the film and used to monitor orientation uniformity in the machine direction. Similarly, it can be mounted above a running yarn line and used to observe any periodic orientation effects. In addition to such on-line usages, the instrument can also be fixed in place and used in the off-line examination of polymeric products.

As shown in FIG. 7, the analytical signal from the fluorescence sensor, PMT 60, passes to a synchronous demodulator 80 through preamplifier 66a and amplifier 82. Associated with PMT 60 and preamplifier 66a, there is a gain control circuit including differentiating and control elements 84, 86 of the type disclosed by Lehtinen in U.S. Pat. No. 3,525,871. With such a gain control circuit, the dc component is stabilized and the output signal from the PMT is, accordingly, proportional to the Vac/Vdc ratio. The dc component of the bias-stabilized, composite signal is blocked by a capacitor 88. The remaining ac signal is represented by waveform 90 in FIG. 8 A. Noise has been omitted in this representation to facilitate comparisons with the waveforms of FIGS. 8 B–D. A representation of the actual output of capacitor 88, including noise components, is shown at 91 in FIG. 8 E. In synchronous demodulator 80, such a signal is full-wave rectified by inverting the alternate half-cycles at each of the zero-crossing points signalled by the phase-adjusted, synchronous, reference signal on conductor 92. Put differently, the ac component is synchronously demodulated at the same frequency as the reference signal. As illustrated, demodulator 80 is an operational amplifier that is switched between inverting and noninverting configurations. The full-wave-rectified output of demodulator 80, waveform 93 (FIG. 8 D), is the input to a low-pass, filter averager 94 which yields the averaged, analytical signal Dex directly. The manner in which the reference signal analog on conductor 92 is kept in exact phase relationship with the analytical signal obtained from PMT 60 is explained below.

The sinusoidal reference signal from photodiodes 61 advances to a multi-stage, voltage-controlled, phase-shifting circuit 95 via preamplifier 66r. The second input to circuit 95 is based on the output of amplifier 82 which is fed in tandem to a synchronous demodulator 96. As illustrated, demodulator 96 is an operational amplifier that is switched between inverting and noninverting configurations. A zero-crossing comparator 98 receives the output of phase-shifting circuit 95 and is connected to demodulator 96 to invert alternate half-cycles of the analytical signal at the phase quadrature points of the phase-adjusted reference signal. A typical waveform is shown at 100 in FIG. 8 B. Such a signal is fed to an integrator 102 to produce a running-average-type control signal which is amplified at 104 and fed back to phase-shifting circuit 95. Thus, the output of circuit 95 is caused to be in phase quadrature with the analytical signal from amplifier 82. As illustrated, integrator 102 includes an operational amplifier, a feedback capacitor, an input resistor and an electronic switch. The latter switch is closed momentarily, before starting a measurement cycle, to discharge the capacitor and thereby provide a reset. In the test embodiment, the electronic switch in integrator 102 is closed by a limit switch 105 as head 14 passes over the edge of film 12 at the end of a scanning traverse.

In a fixed, 90° phase-shifter 106, the output of circuit 95 is adjusted to match precisely the phase of the analytical signal. The output of circuit 106 is connected to a zero-crossing comparator 108 which, internally, is configured to produce on-off squarewave signals, waveform 110 (FIG. 8 C), characteristic of the times that the in-phase sinusoidal analog of the analytical signal is respectively above and below its zero-volt base line. The squarewave 110 is applied to the synchronous demodulator 80 and to 0°–360° phase-detector 112 in phase-measuring circuitry 72.

The output of demodulator 96 is balanced, as shown by inverted waveform 100 in FIG. 8 B, only when the control signal output of comparator 98 is in exact phase-quadrature with waveform 90, i.e., only when the output of comparator 108 is locked in phase with the analytical signal. The fluorescence polarization instrument may be caused to traverse the width of a moving polymeric web. In this case, the direction of orientation changes and the phase of the signal output of amplifier 82 leads or lags with respect to the phase of the reference signal to cause a positive or negative imbalance in the symmetry of waveform 100, i.e., in the output of demodulator 96. In response, integrator 102 generates a corresponding phase-adjustment signal for phase-shifting circuit 95. With this circuitry, values of $\theta$ can be determined within about 0.2° over a 180° range of directionality for the polarization vector. When the outputs of amplifier 82 and comparator 108 are again in phase, the output of demodulator 96 is balanced, as shown in FIG. 8 B, waveform 100. At that time, the net input to integrator 102 is zero. In these respects, it is noted that the set point of amplifier 104, as determined by resistor 114, permits a phase-shift range of ±400°. Theoretically, the analytical signal can lag or lead the reference signal by as much as 360°.

The phase-measuring circuitry 72 includes a zero-crossing comparator 118, the phase detector 112 and a low-pass filter 120. The sinusoidal reference signal from preamplifier 66r is converted to a square waveform by comparator 118. This signal and the phase-modified signal 110 from phase-shifting circuitry 70 are inputs to phase detector 112. Phase detector circuit 112 comprises a switched exclusive OR gate 122 in series connection with two "D" type flip-flops 124 and 126. A double-throw switch 128 connected to one terminal of exclusive OR gate 122 serves to invert the state of the logic signal input to terminal C of flip-flop 124, which is configured as a divide-by-two element. In flip-flop 124, terminals R and S are inactive and terminals D and $\overline{Q}$ are connected together. The Q terminal is connected to the reset R terminal of flip-flop 126 which has its D terminal connected to +15 v and its set terminal S inactive. The C terminal of flip-flop 126 is connected via branch point 129 to the output terminal of zero-crossing comparator 108 and the Q output terminal is connected to the input terminal of low-pass filter 120. With flip-flop 126 configured in this manner, it passes the analytical signal analog 110 to filter 120 only during a gating period following each positive half-cycle of the reference analog from flip-flop 124. Low-pass filter circuit 120 includes a capacitor in combination with a resistor at the non-inverting terminal of an operational amplifier 130, typically a type 142601. The output of amplifier 130 is scaled by a variable resistor 131.

Switch 128 is controlled by the operator and is positioned according to the direction of the last stretch imparted to film 12. In FIG. 7, the switch is in the MD position because the test embodiment was located beyond the MD stretching zone for film 12. If the apparatus were to be located beyond a zone where film is stretched in the transverse direction (TD), switch 128 would be moved to its TD position.

In FIGS. 9 A–D, the squarewave output 110 of comparator 108 is shown with the output 136 of flip-flop 124 and the output 138 of flip-flop 126 for various phase relationships of the reference and analytical signals.

FIG. 9 A shows the condition when reference signal analog 136 and analytical signal analog 110 are in phase agreement. This results in a balanced difference signal 138 with shaded areas that correspond to the full extent of the gating periods. FIG. 9 B shows a 90° phase lag of the analytical signal analog 110 from the reference signal analog 136, wherein the shaded areas of difference signal 138 correspond to three-fourths of the full extent of the gating period. FIG. 9 C shows the analytical signal lagging the reference signal by 270°. FIG. 9 D shows the analytic signal lagging the reference signal by almost a full cycle. This is a situation which could exist, for example, with the apparatus located beyond an MD stretching zone and switch 128 in its TD position. In this situation, the difference signal would be ambiguous as it changes state rapidly between the representations shown in FIGS. 9 A and 9 D. Switch 128 is then used to provide a 180° phase shift to the reference signal to enable continuous unambiguous readings through this cross-over point.

The phase difference between the analytical and reference signals is determined by measuring the average voltage in the rectangular signal 138 at the output of flip-flop 126 in the following manner. The sinusoidal reference signal at branch point 132 (FIG. 7) is converted to squarewave form by zero-crossing comparator 118 before it is input through exclusive OR gate 122 to clock flip-flop 124. Referring to FIGS. 9 A–D, it is apparent that the high-going edges of the squarewave output 136 of flip-flop 124 serves as a gate to control the turn-off times of the phase difference waveform 138 once turned on by the high-going edges of the analytical squarewave signal 110. The figures clearly depict the linearity of the average signal power result (area under the curve) as a function of phase angle which is provided by the circuit.

As noted above, switch 128 is used to provide a 180° phase shift to the reference squarewave signal when measurements about the indeterminant angles of 0° and 360° become ambiguous.

Five cascaded stages of phase-shifting for the reference signal are shown schematically in FIG. 7. Referring to FIG. 10, each stage includes an amplifier 140 controlled by a light-emitting diode (LED) 142. The series-connected LEDs receive the biasing output of amplifier 104 associated with integrator 102 (FIG. 7). As noted above, circuit 95 insures continuity of phase-lock, between the analytical signal and the phase-adjusted reference signal analog from comparator 108, over the theoretical range of ±360°.

Instead of the gain control components shown at 84, 86 in FIG. 7, a circuit for generating an implicit ratio of the composite (ac+dc) signal from the detector can be used. Such a circuit is shown in FIG. 11 and has been described by Faulhaber in U.S. Pat. No. 3,955,096. In this embodiment, the composite signal from preamplifier 66a' is applied to the noninverting terminal of operational amplifier 144. An optical isolator 146 is attached to the inverting terminal and controls the current flow through a feedback resistor 148. The output of amplifier 144 is connected to capacitor 88' and to the inverting terminal of an amplifier 150. A voltage-dividing network 152 provides a dc reference voltage which is summed with the output of amplifier 144. The difference is integrated in amplifier 150 which generates the input to optical isolator 146. This circuit is particularly suitable for use with a photodiode detector, or with a PMT with a fixed level of high voltage supply.

What is claimed as new and desired to be secured by Letters Patent is:

1. An apparatus comprising:
   means for establishing a beam of rotating linearly polarized light incident on a product to be inspected;
   a fixed polarizer in and partially intercepting the path of said linearly polarized light;
   a first photodetector having a light sensitive element in the path of light passing through said fixed polarizer;
   a second photodetector having a light sensitive element in the optical path of light emitted from the product; and
   a detection circuit connected to said first and second photodetectors, the latter providing synchronous and sinusoidal reference and analytical signals, respectively, to said detection circuit, said detection circuit comprising:
      first circuitry for adjusting the phase of the reference signal into agreement with the phase of the analytical signal and
      second circuitry for the synchronous demodulation of the analytical signal,
      said reference signal being an input to the first circuitry, said analytical signal being an input to both circuitries and the phase-adjusted output of said first circuitry being an input to the second circuitry.

2. The apparatus of claim 1 wherein is provided an emission housing in said incident beam and a filter in the housing in the path of emitted light, the optical paths of the incident and emitted light being coaxial.

3. The apparatus of claim 1, said detection circuit further comprising third circuitry for measuring phase differences between the reference signal and the phase-adjusted reference signal, said reference and phase-adjusted signals being inputs to the third circuitry.

4. An apparatus comprising:
   means for establishing a beam of rotating linearly polarized light incident on an advancing polymeric film;
   an emission housing in and partially intercepting said incident beam;
   a fixed polarizer on said emission housing;
   a filter in the emission housing in the path of light emitted from the film, the optical paths of said incident and emitted light being coaxial;
   a first photodetector having a light sensitive element in the path of incident light passing through said fixed polarizer;
   a second photodetector having a light sensitive element in the path of emitted, filtered light; and
   a detection circuit connected to said first and second photodetectors, the latter providing synchronous and sinusoidal reference and analytical signals, respectively, to the detection circuit, said apparatus further comprising:
      a support housing for said means and said emission housing; and
      means mounting the support housing above and for traversing movement relative to the path of advance for said film.

* * * * *